(12) United States Patent
Zhang et al.

(10) Patent No.: US 11,685,730 B2
(45) Date of Patent: Jun. 27, 2023

(54) CYCLIC COMPOUND FORMED BY FRIEDEL-CRAFTS REACTION AT POSITIONS 1 AND 3 OF CARBAZOLE AND PREPARATION METHOD THEREOF

(71) Applicant: Nanjing University of Posts and Telecommunications, Nanjing (CN)

(72) Inventors: Guangwei Zhang, Nanjing (CN); Jiayin Xiang, Nanjing (CN); Wei Huang, Nanjing (CN); Chuang Gao, Nanjing (CN); Linghai Xie, Nanjing (CN); Xinru Zhi, Nanjing (CN)

(73) Assignee: Nanjing University of Posts and Telecommunications, Nanjing (CN)

( * ) Notice: Subject to any disclaimer, the term of this patent is extended or adjusted under 35 U.S.C. 154(b) by 0 days.

(21) Appl. No.: 17/329,654

(22) Filed: May 25, 2021

(65) Prior Publication Data
US 2022/0041580 A1    Feb. 10, 2022

(30) Foreign Application Priority Data
Aug. 5, 2020    (CN) .......................... 202010775034.3

(51) Int. Cl.
C07D 403/10    (2006.01)
(52) U.S. Cl.
CPC .................................. C07D 403/10 (2013.01)
(58) Field of Classification Search
CPC ................................................... C07D 403/10
See application file for complete search history.

(56) References Cited

PUBLICATIONS

Registry No. 2545619-50-7 File Registry on STN Dec. 4, 2020.*

* cited by examiner

*Primary Examiner* — Rebecca L Anderson
(74) *Attorney, Agent, or Firm* — Cook Alex Ltd.

(57) ABSTRACT

A cyclic compound formed by a Friedel-Crafts reaction at positions 1 and 3 of carbazole and a preparation method thereof are disclosed. The compound is formed by connecting an achiral type I di-(tertiary alcohol) synthon constructed from fluorenyl and benzene or a derivative thereof, at position 9 of fluorenyl with positions 1 and 3 of carbazole, forming a closed ring structure with a clear and durable shape, having clear side lengths and vertices on the nanometer scale. The cyclic compound has a general structural formula of

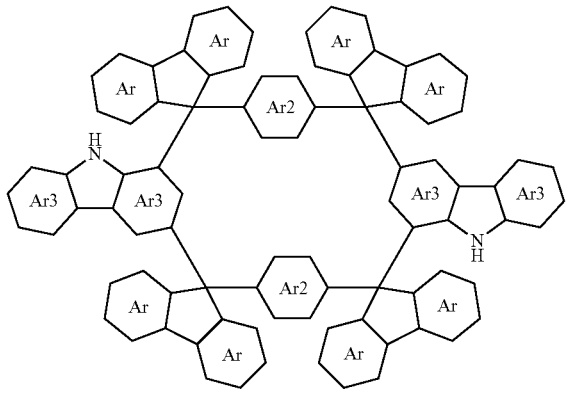

2 Claims, 6 Drawing Sheets

CYCLIC COMPOUND FORMED BY FRIEDEL-CRAFTS REACTION AT POSITIONS 1 AND 3 OF CARBAZOLE AND PREPARATION METHOD THEREOF

CROSS-REFERENCE TO RELATED APPLICATION(S)

The application claims priority to Chinese Application No. 202010775034.3, filed on Aug. 5, 2020, entitled "Cyclic Compound Formed By Friedel-Crafts Reaction At Positions 1 And 3 Of Carbazole And Preparation Method Thereof", which is hereby incorporated by reference in its entirety.

FIELD OF THE INVENTION

The present disclosure relates to the technical field of organic semiconductor materials, and specifically relates to a cyclic compound formed by a Friedel-Crafts reaction at positions 1 and 3 of carbazole and a preparation method thereof.

In 2014, the research group of Professor Linghai Xie proposed a novel structurally rigid nano-scale three-dimensional closed-ring structure—organic nano grid (L. Wang, G.-W. Zhang, C.-J. Ou, L.-H. Xie, J.-Y. Lin, Y.-Y. Liu, and W. Huang, Org. Lett., 2014, 16, 1748-1751). As can be seen from the analysis of geometric structure, the grid is a closed-ring structural unit different from a large ring, having obvious edges and corners, vertices and side lengths. Although some macrocyclic compound structures having regular edges and corners have also been reported, in fact, polygonal-ring macrocyclic compound with a regular shape have not attracted the attention of scientists. However, the three-dimensional grid is the basis for the construction of many complex structures, such as multi-step structures, "Tian"-shaped grids and many complex grid topologies. In addition to the shape, the grid is more extensible than the macrocycle. The edges or vertices of the grid are used to interconnect the molecular grid unit in various ways.

Since 2014, the group of Linghai Xie has been committed to researching different types of nanogrids, which can be classified into "Kou"-shaped, "Ri"-shaped, trapezoid, windmill, prismatic nanogrids, etc. However, it is found that this kind of grid may be chiral due to a potential chirality of position 9 in fluorenyl, and a large number of chiral isomers would be formed in the non-stereoselective grid reaction, resulting in low synthesis yield and difficult separation. In order to overcome this shortcoming, an achiral nanogrid with rigid structure was designed and constructed.

In order to construct such molecules, a class of achiral type I di-(tertiary alcohol) synthons was synthesized. With a series of type I tertiary alcohol synthons, on the basis of Friedel-Crafts reaction, positions 1 and 3 of carbazole are connected to position 9 of fluorene, to obtain an achiral ring-closed structure. This reaction breaks the way of closing ring at positions 3 and 6 of carbazole in the previous Friedel-Crafts reactions, and makes it possible to realize a new method of closing ring at positions 1 and 3 of carbazole in a simple way. The method achieves the preparation of such grid structure, is free of metal catalyst, is environmentally friendly, and/or is atom economically.

SUMMARY OF THE INVENTION

An objective of the present disclosure is to provide a cyclic compound formed by a Friedel-Crafts reaction at positions 1 and 3 of carbazole, with a regular structure and excellent performance, and a preparation method thereof.

The present disclosure provides a cyclic compound formed by a Friedel-Crafts reaction at positions 1 and 3 of carbazole, in which, an achiral type I di-(tertiary alcohol) synthon constructed from fluorenyl and benzene or a derivative thereof, is connected at position 9 of fluorenyl with positions 1 and 3 of carbazole, forming a closed ring structure with a clear and durable shape, having clear side lengths and vertices on the nanometer scale. Due to the obvious attributes of length, width and height, the molecule is more rigid, and has a general structural formula of

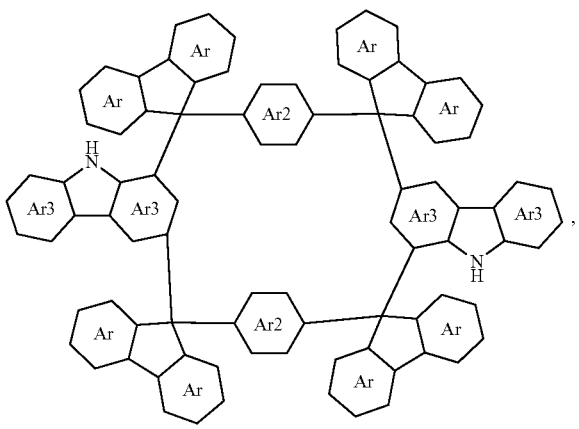

in which

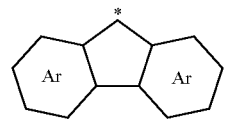

is a radical of fluorene or a derivative of fluorene,

is a radical of benzene or a derivative of benzene, and

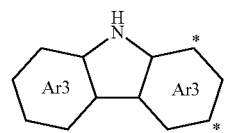

is a radical of carbazole or a derivative of carbazole.

In some embodiments,

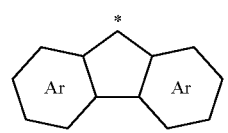

is selected from the group consisting of

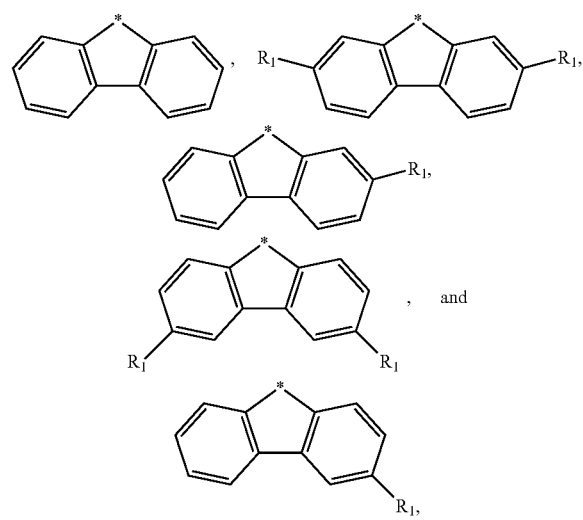

wherein $R_1$ is selected from the group consisting of alkoxy, alkyl (preferably $C_{1-10}$ alkyl), and halogen.

In some embodiments,

is selected from the group consisting of

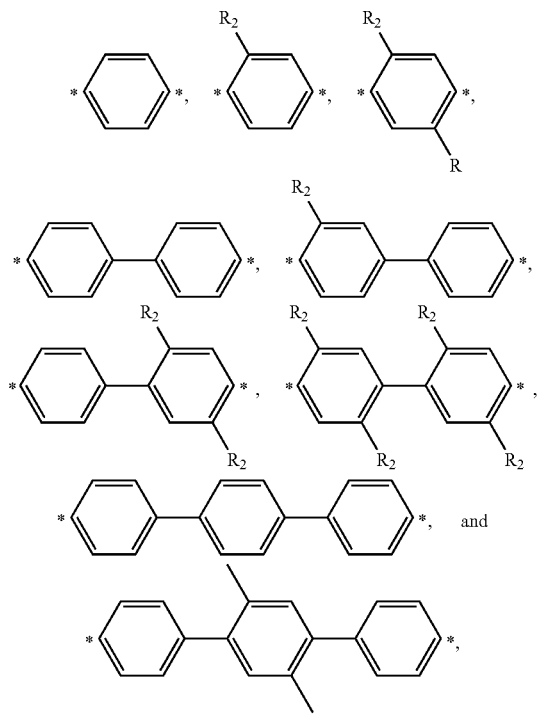

wherein $R_2$ is selected from the group consisting of alkoxy, and alkyl containing not more than 5 carbon atoms.

In some embodiments, the derivative of carbazole is unsubstituted at positions 1, 3, and NH of carbazole.

In some embodiments, the derivative of carbazole is selected from the group consisting of

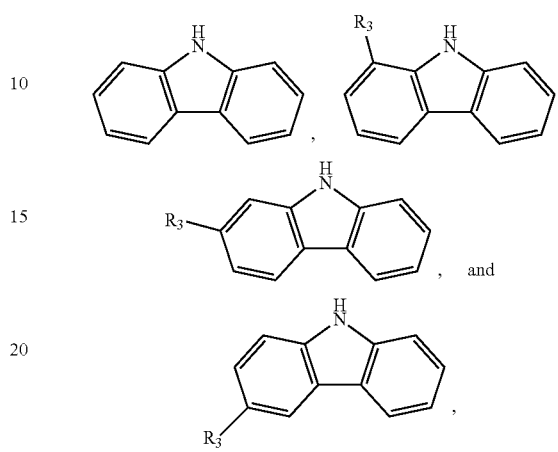

wherein $R_3$ is selected from the group consisting of alkoxy, alkyl (preferably $C_{1-10}$ alkyl), Br and Cl.

In some embodiments, the alkyl is tert-butyl.

A method for preparing the cyclic compound formed by a Friedel-Crafts reaction at positions 1 and 3 of carbazole, comprising,

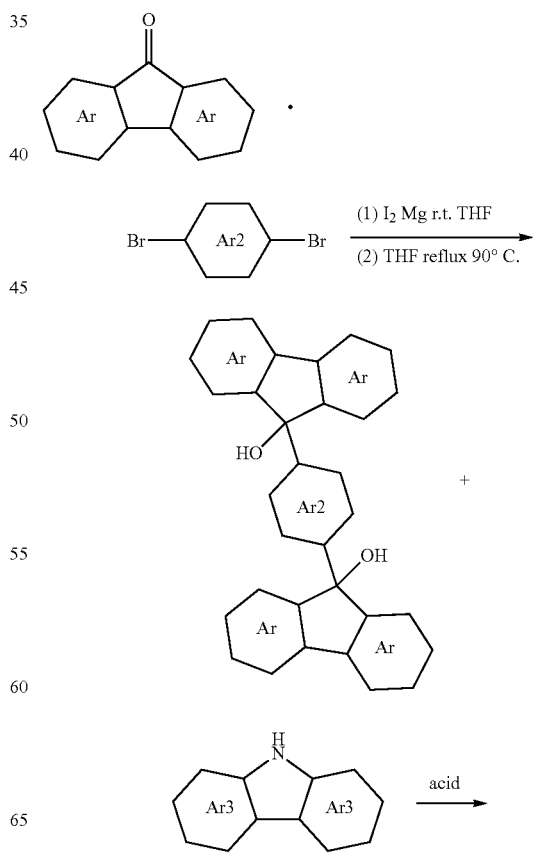

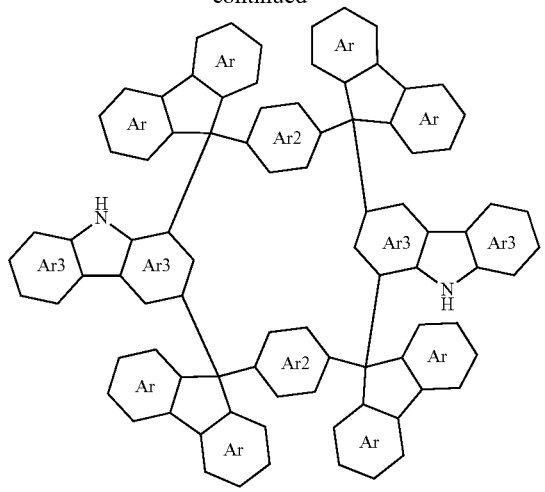

a first step of synthesizing a Grignard reagent from p-bromobenzene or a derivative thereof, and reacting the Grignard reagent with fluorenone or a derivative thereof to obtain a type I di-(tertiary alcohol) synthon; and a second step of adding a catalyst to the type I di-(tertiary alcohol) synthon at ambient temperature, and reacting the resulting mixture with carbazole or a derivative thereof in a dry organic solvent, to obtain a cyclic compound formed by a Friedel-Crafts reaction at positions 1 and 3 of carbazole.

In some embodiments, in the first step, a molar ratio of magnesium particles:p-bromobenzene or a derivative thereof:luorenone or a derivative thereof is 3:1:2.5.

In some embodiments, synthesizing a Grignard reagent from p-bromobenzene or a derivative thereof in the first step is performed at 60° C. for 7 hours, to obtain a Grignard reagent, and reacting the Grignard reagent with fluorenone or a derivative thereof to obtain a type I di-(tertiary alcohol) synthon is performed at 90° C. for 24 hours, to obtain the type I di-(tertiary alcohol) synthon.

In some embodiments, a molar ratio of the type I di-(tertiary alcohol) synthon:carbazole or a derivative thereof: the catalyst is 1:1:10, wherein the catalyst is at least one selected from the group consisting of Lewis acid, trifluoromethanesulfonic acid, and boron trifluoride ether.

The structure of the target compound has been confirmed by nuclear magnetic resonance (NMR), matrix-assisted laser analysis time-of-flight mass spectrometry (MALDI-TOF-MS), and X-ray diffraction (XRD) pattern.

Some embodiments of the present disclosure have the following advantages:

(1) A new type of molecule: a new grid-like structure is formed by subjecting tertiary alcohol synthon and carbazole to a Friedel-Crafts reaction, in which, position 9 of fluorene and positions 1 and 3 of carbazole are connected. This reaction breaks the previous mode of reaction at positions 3 and 6 of carbazole, and has the advantages of easy expansion and synthesis. Compared with the products from the closed ring reaction at positions 3 and 6 of carbazole, the compound obtained by this reaction has a better solubility, which makes subsequent research convenient (Note: In this reaction, carbazole or a derivative thereof refers to a molecule that is unsubstituted at position NH of carbazole; for molecule(s) that is substituted at position NH of carbazole, only products of closed ring reaction at positions 3 and 6 of carbazole could be obtained under the same reaction conditions);

(2) In terms of synthesis method: the reaction is a Friedel-Crafts cyclization reaction, which is performed under mild conditions, and is simple in operation, low in toxicity, low in cost, high in yield, and environmentally friendly;

(3) In terms of structure: the compound according to the present disclosure is a class of molecules without isomers, by avoiding the potential chirality at position 9 of fluorenyl; the structure thereof is characterized by a durable shape, clear edges and corners, and multiple expansion sites, and could be applied to supermolecular applications such as ions recognition;

(4) The compound according to the present disclosure has a regular structure, adjustable molecular aperture size, great rigidity, and an adjustable electronic energy level, which is suitable for solution processing, and has expanded application range of materials;

(5) The fluorene-based grid has a good optical, thermal and electrochemical stability; and is a kind of nano-scale grid semiconductor with different photoelectric properties, potential high mobility, and great luminescence properties.

DETAILED DESCRIPTION OF ILLUSTRATIVE EMBODIMENTS

Figure 1:
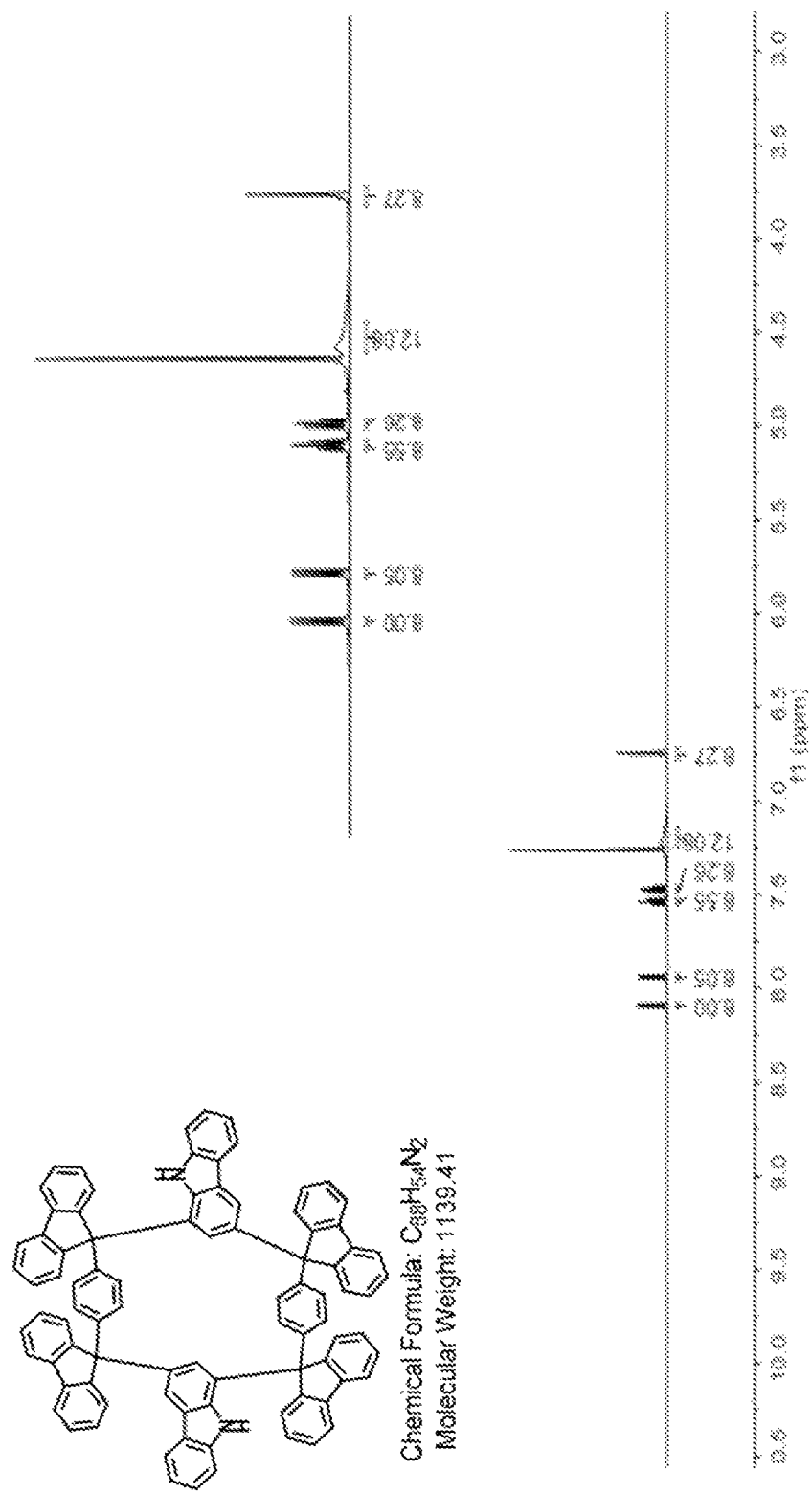
FIG. 1 shows a hydrogen nuclear magnetic resonance spectrum of the cyclic compound DBCZ as prepared in Example 3.
Figure 2:
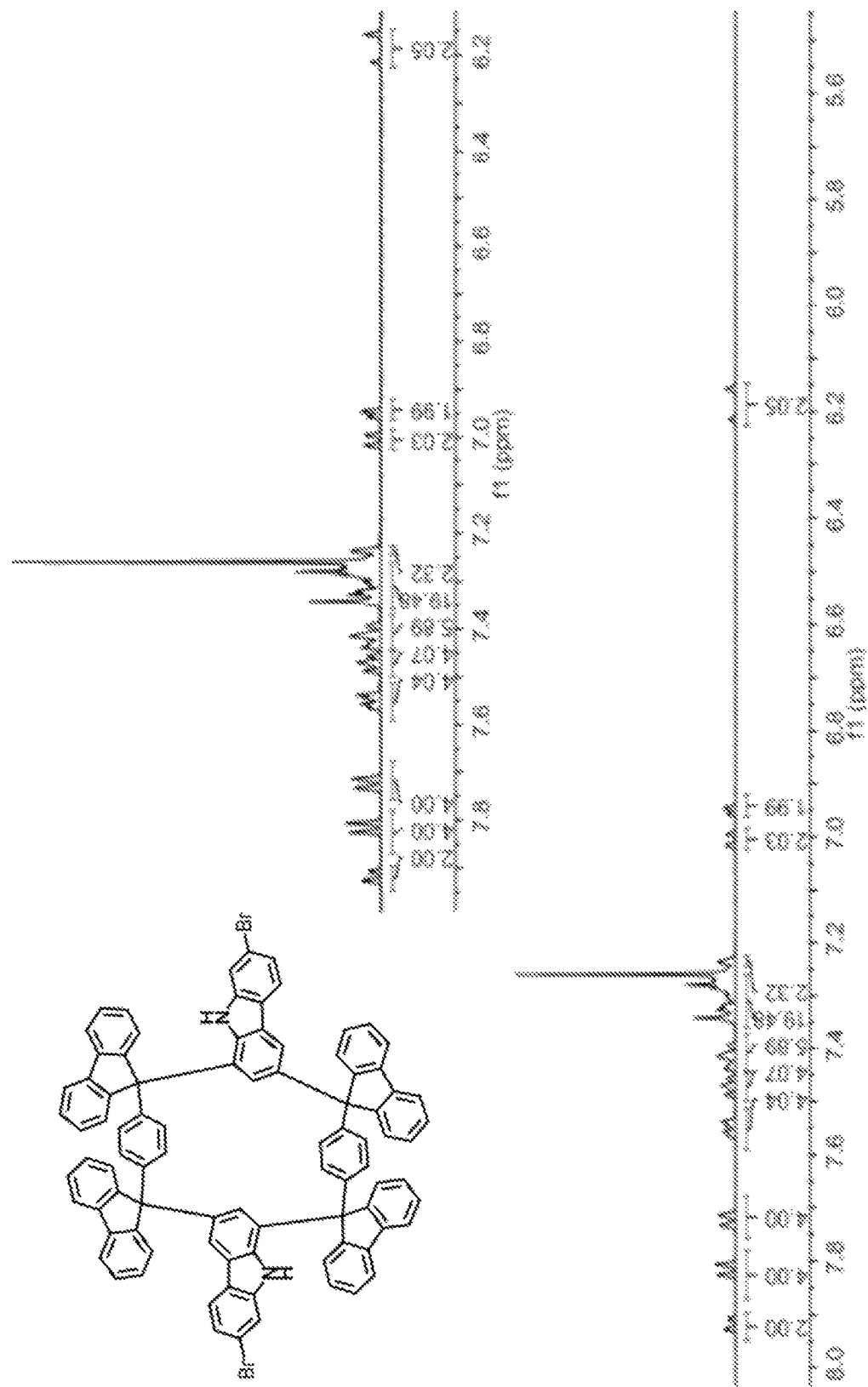
FIG. 2 shows a hydrogen nuclear magnetic resonance spectrum of the cyclic compound 2-BrDBCZ as prepared in Example 4.
Figure 3:
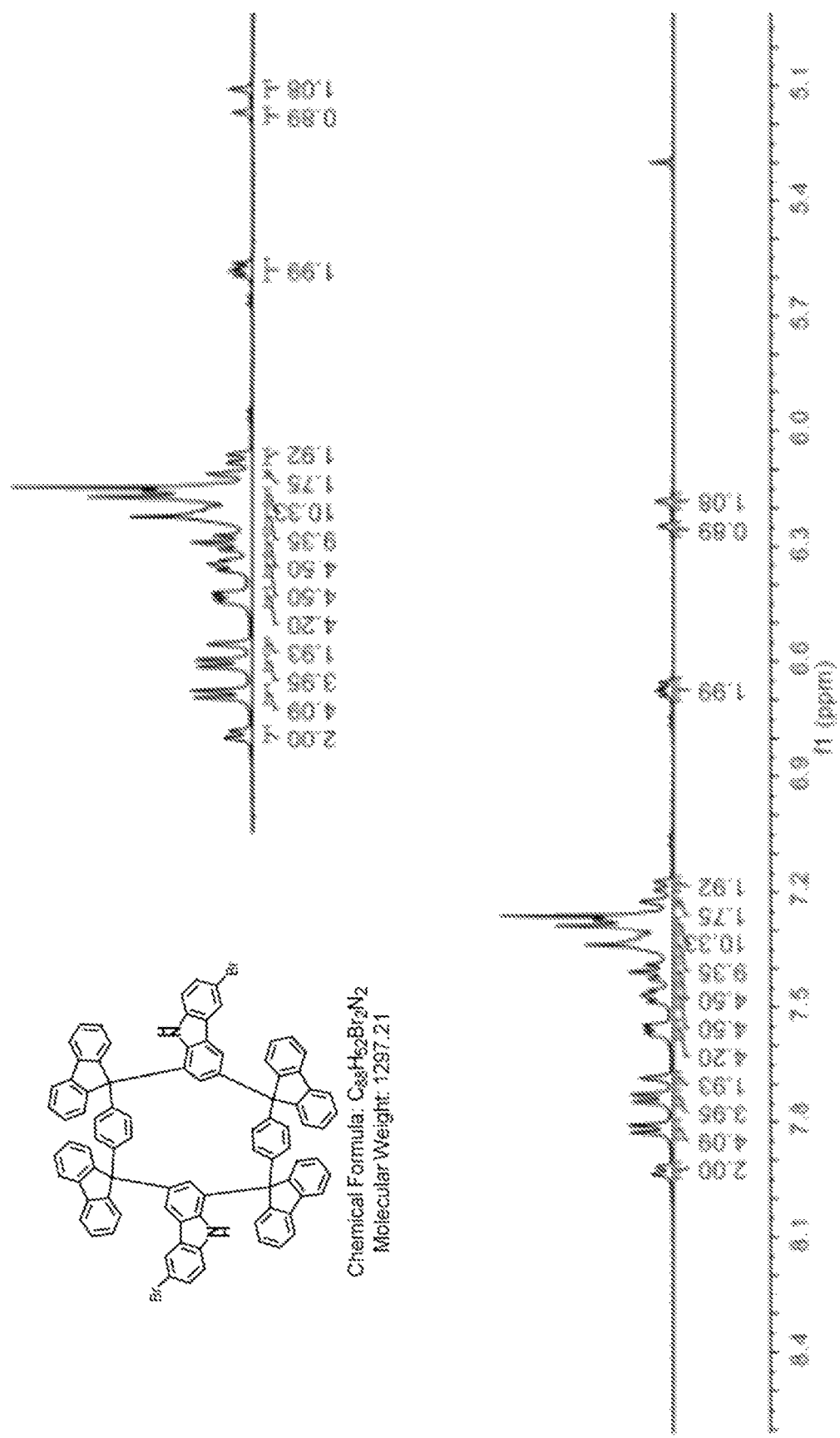
FIG. 3 shows a hydrogen nuclear magnetic resonance spectrum of the cyclic compound 3-BrDBCZ as prepared in Example 5.
Figure 4:
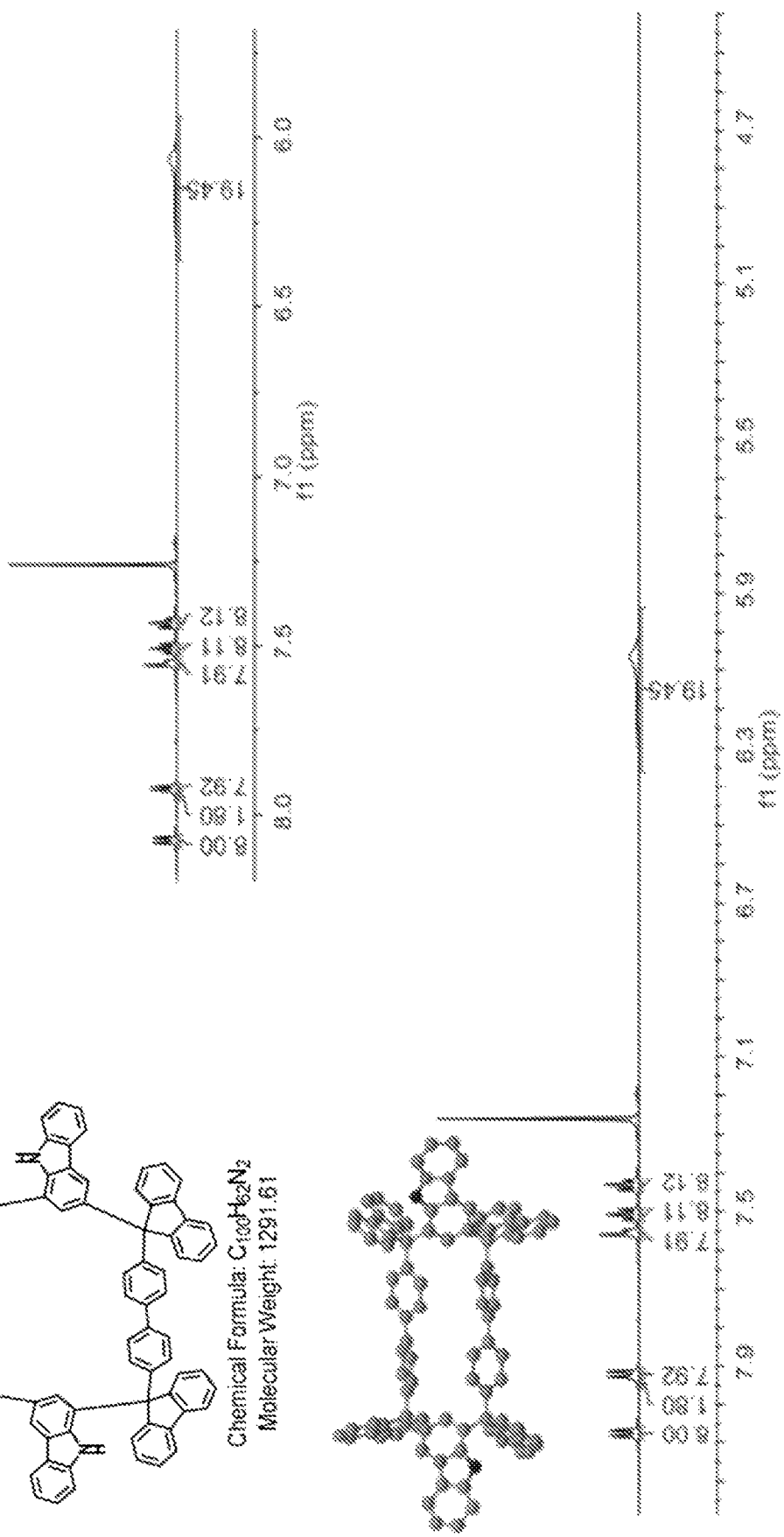
FIG. 4 shows a hydrogen nuclear magnetic resonance spectrum of the cyclic compound LBCZ as prepared in Example 6.
Figure 5:
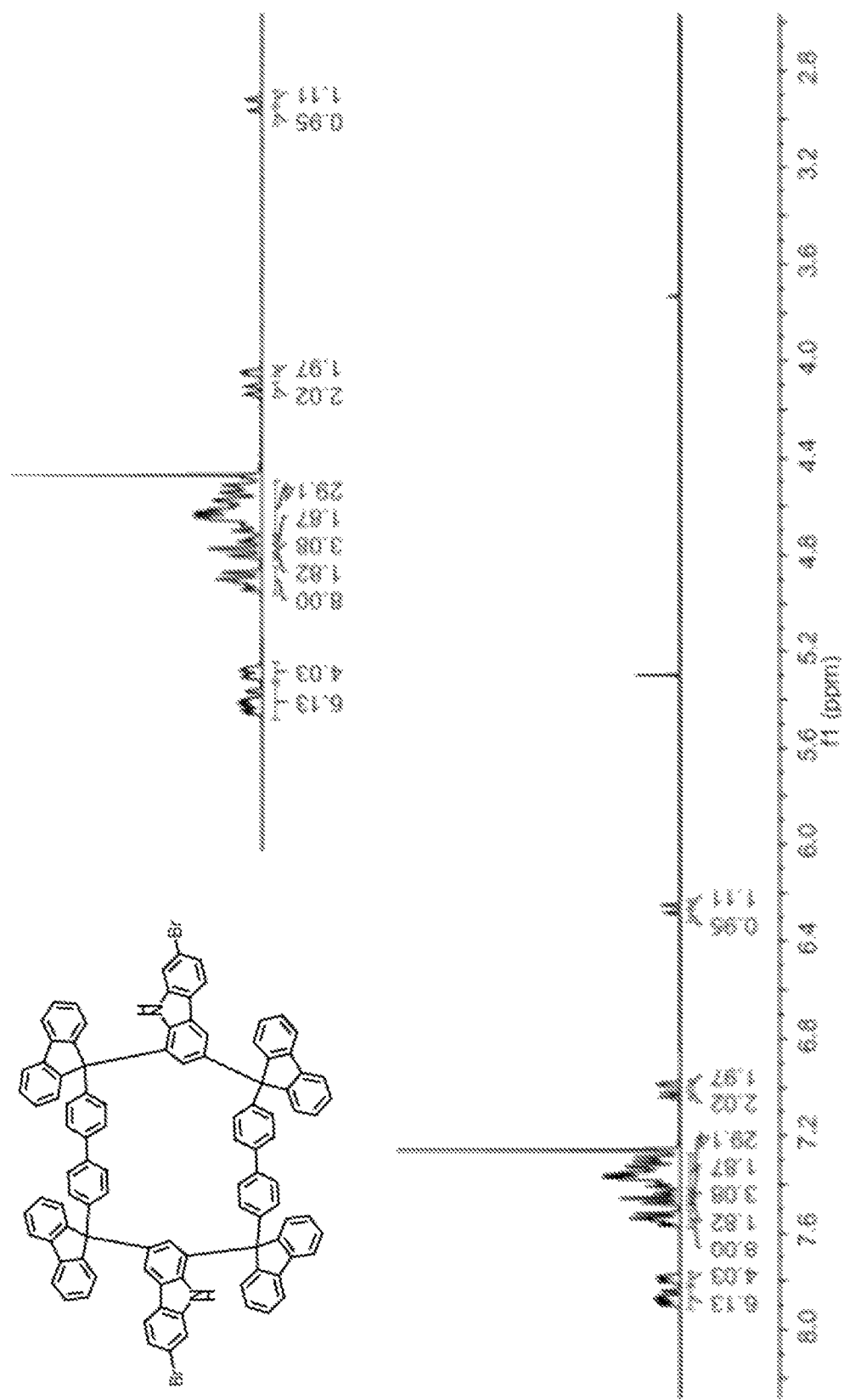
FIG. 5 shows a hydrogen nuclear magnetic resonance spectrum of the cyclic compound 2-Br LBCZ as prepared in Example 7.
Figure 6:
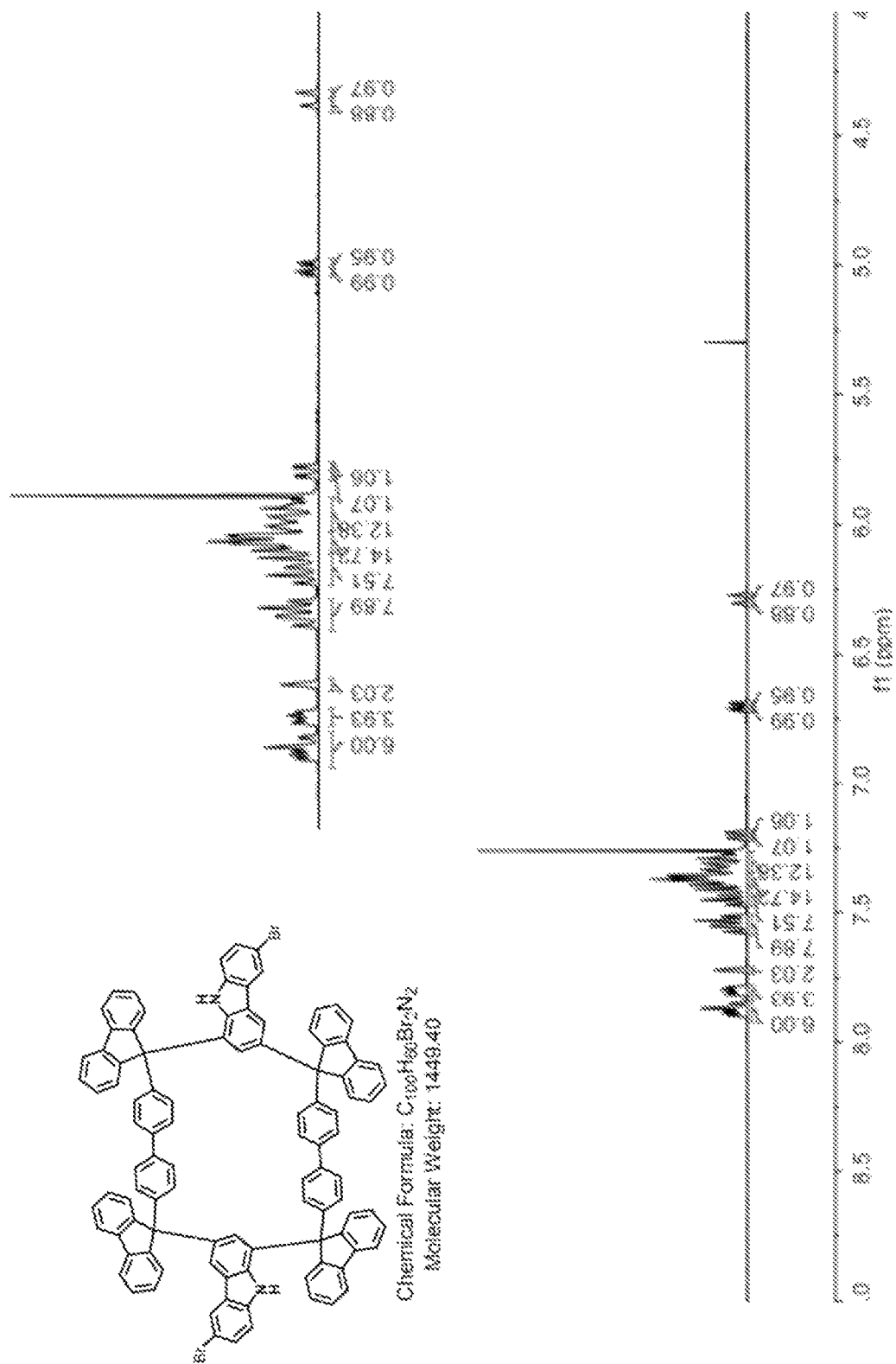
FIG. 6 shows a hydrogen nuclear magnetic resonance spectrum of the cyclic compound 3-Br LBCZ as prepared in Example 8.

The present disclosure provides a method for preparing the cyclic compound formed by a Friedel-Crafts reaction at positions 1 and 3 of carbazole, comprising, step 1, synthesizing a Grignard reagent from p-bromobenzene or a derivative thereof, and reacting the Grignard reagent with fluorenone or a derivative thereof to obtain a type I di-(tertiary alcohol) synthon; and step 2: reacting the type I di-(tertiary alcohol) synthon at ambient temperature with carbazole or a derivative thereof in a dry organic solvent at the present of an acid as a catalyst, to obtain a cyclic compound formed by a Friedel-Crafts reaction at positions 1 and 3 of carbazole.

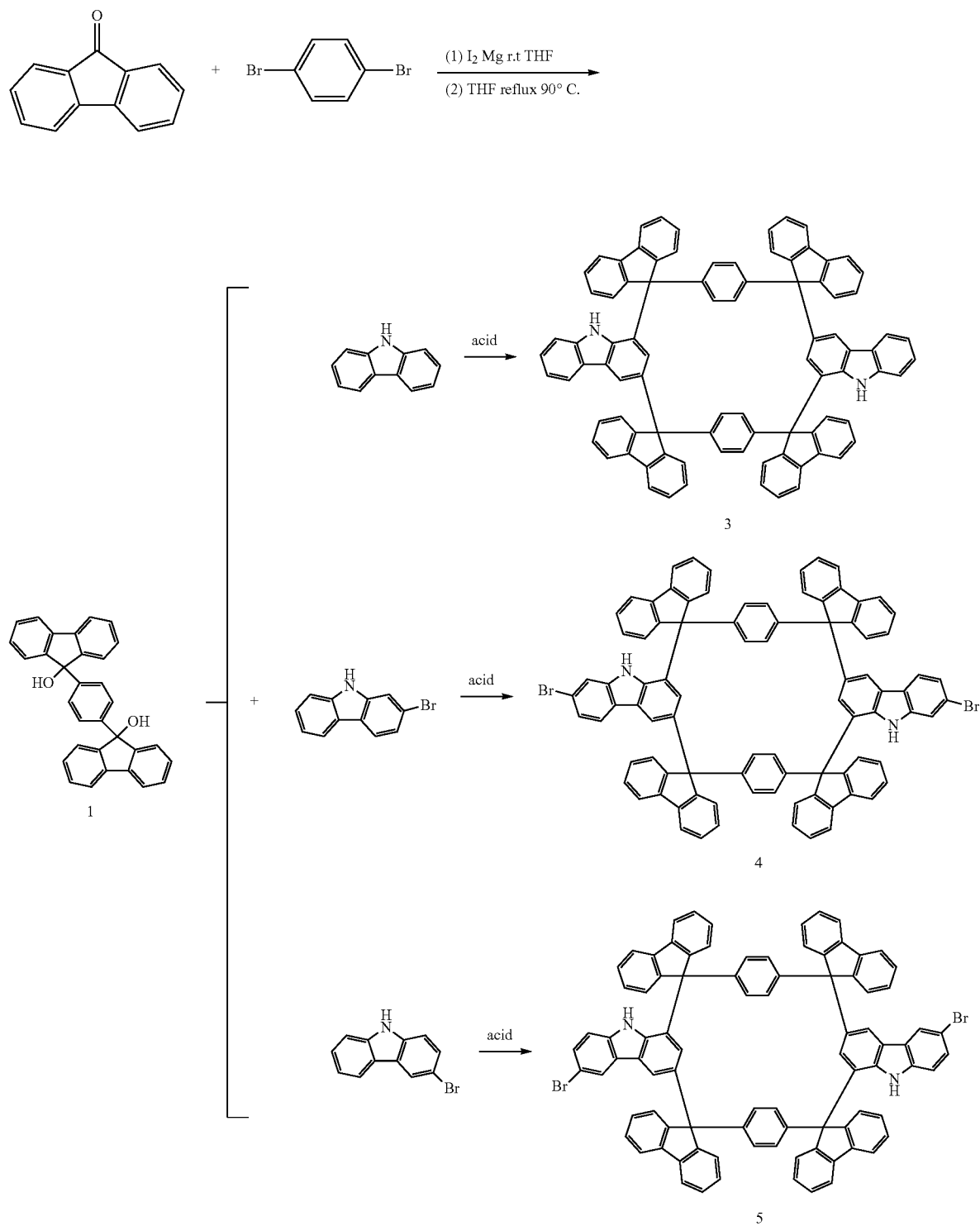
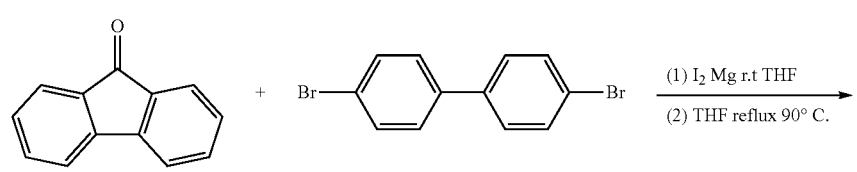

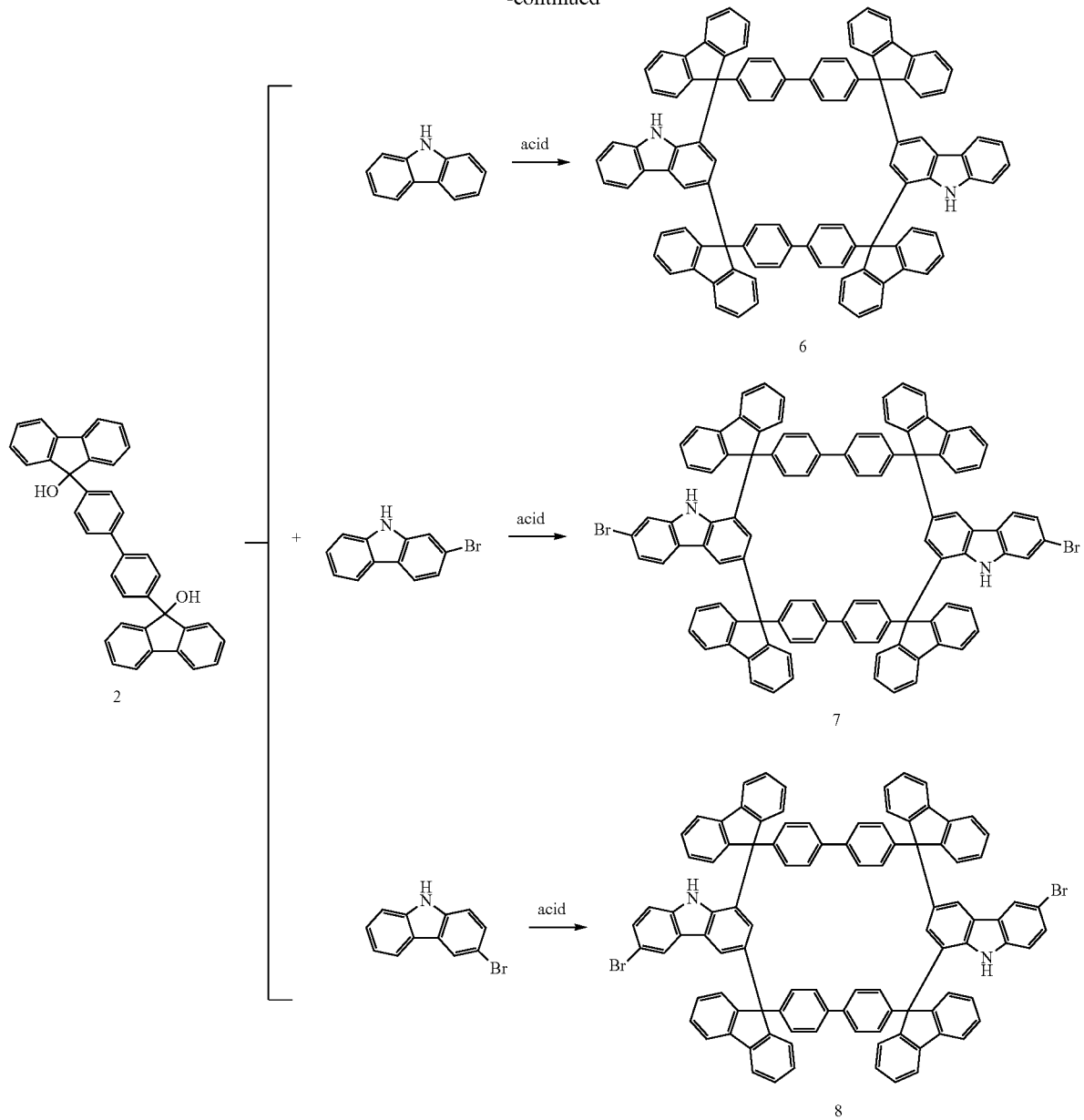

The technical solutions are further described below in conjunction with examples. However, these examples do not limit the implementation of the present disclosure. The present disclosure has many different implementation modes and is not limited to the content explicitly described in this specification. As long as those skilled in the art do not violate the spirit of the present disclosure, the implemented technical solution should fall within the scope of the present disclosure.

Example 1

Preparation of Type I Tertiary Alcohol Synthon 1:DBD-FOH

All the glass instruments to be used (magnons, long needles, 2 two-necked flasks, and 2 spherical condensers) were dried in advance. Tetrahydrofuran (THF) was distilled in advance (during the distillation of THF, a small amount of benzophenone was added for color development; when there was no water in the flask, THF in the flask turned dark blue, and at this time THF was collected for experiments). Then the glass instruments were assembled, and magnesium particles (3.06 g, 0.127 mol) and iodine particles (2.54 mg, 0.02 mmol) were added to one set of the glass instruments, then the glass instruments were sealed with vacuum grease and sealing tape, and the system was vacuumed three times, and protected by a nitrogen balloon. 1,4-dibromobenzene (10 g, 0.042 mol) in a container, which had been vacuumed and filled with nitrogen, was dissolved with the distilled THF (60 mL), and 5 mL of the resulting 1,4-dibromobenzene solution was injected into the reactor (in the set of the glass instruments) with a syringe at a temperature of an ice-water bath, and hot air was blown to initiate the reaction. Then the mixture was put in an oil bath at 60° C., the remaining 1,4-dibromobenzene solution (1,4-dibromobenzene solution not-added) was slowly added, and the resulting mixture was stirred for 7 hours until the reaction was completed. Then another glass instrument was assembled; fluorenone (19.14 g, 0.106 mol) was weighed and added thereto, and the system was vacuumed three times, and protected by a nitrogen ball; the distilled THF (30 mL) was injected to dissolve fluorenone. When the above reaction was completed (a. the product Grignard reagent was purple-black, which was colored by iodine in the solution; b. when the Grignard reagent was consumed by the reaction, there may be a small amount of magnesium chips at the bottom of the flask, mostly in powder form), the fluorenone-loaded device (the set of glass instruments loaded with fluorenone) was placed in an oil bath and heated to 90° C., then a small amount of THF and the liquid from the previous reactions were slowly added, and stirred for 24 hours to obtain a tertiary alcohol solution. When the temperature dropped to room temperature, the reaction was quenched with saturated $NH_4Cl$ solution, to obtain a golden yellow solution, then the golden yellow solution was extracted with $CH_2Cl_2$ several times. The organic phase was collected, dried with anhydrous magnesium sulfate, filtered out the desiccant, and distilled under reduced pressure to remove the solvent, to obtain a crude product. The crude product was further purified by silica gel column chromatography, to obtain a white solid powder (6.5 g, 40%), which is confirmed by $^1$HNMR with the following data:

$^1$HNMR (400 MHz, DMSO) δ 7.84 (d, J=7.5 Hz, 4H), 7.43-7.38 (m, 4H), 7.32-7.26 (m, 8H), 7.19 (s, 4H), 6.28 (s, 2H).

Example 2

Preparation of Type I Tertiary Alcohol Synthon 2: LBD-FOH

All the glass instruments to be used (magnons, long needles, 2 two-necked flasks, and 2 spherical condensers) were dried in advance. Tetrahydrofuran (THF) was distilled in advance (during the distillation of tetrahydrofuran, a small amount of benzophenone was added for color development, when there was no water in the flask, THF in the flask turned dark blue, and at this time THF was collected for experiments). Then the glass instruments were assembled, and magnesium particles (2.34 g, 0.096 mol) and iodine particles (2.54 mg, 0.02 mmol) were added to one set of the glass instruments, then the glass instruments were sealed with vacuum grease and sealing tape, and the system was vacuumed three times, and protected by a nitrogen balloon. 4,4'-dibromobiphenyl (10 g, 0.032 mol) in a container, which had been vacuumed and filled with nitrogen, was dissolved with distilled THF (90 mL), and 5 mL of the resulting 4,4'-dibromobiphenyl solution was injected into the reactor (in the set of glass instruments) with a syringe at a temperature of an ice-water bath, and hot air was blown to initiate the reaction. The mixture was then put in an oil bath at 60° C., the remaining 4,4'-dibromobiphenyl solution (4,4'-dibromobiphenyl solution not-added) were added slowly, and the resulting mixture was stirred for 7 hours until the reaction was completed. Then another set of glass instruments was assembled; fluorenone (14.44 g, 0.08 mol) was weighed and added thereto, and the system was vacuumed three times, and protected by a nitrogen ball; the distilled THF (30 mL) was injected to dissolve fluorenone. When the above reaction was completed (a. the product Grignard reagent was purple-black, which was colored by iodine in the solution; b. when Grignard reagent was consumed by the reaction, there may be a small amount of magnesium chips at the bottom of the flask, mostly in powder form), the fluorenone-loaded device (the set of glass instruments loaded with fluorenone) was placed in an oil bath and heated to 90° C., then a small amount of THF and the liquid from the previous reactions were slowly added, and stirred for 24 hours to obtain a tertiary alcohol solution. When the temperature dropped to room temperature, the reaction was quenched with saturated $NH_4Cl$ solution, to obtain a golden yellow solution, then the golden yellow solution was extracted with $CH_2Cl_2$ several times. The organic phase was collected, dried with anhydrous magnesium sulfate, filtered out the desiccant, and distilled under reduced pressure to remove the solvent, to obtain a crude product. The crude product was further purified by silica gel column chromatography, to obtain a white solid powder (4.5 g, 30%), which is confirmed by $^1$HNMR with the following data:

$^1$HNMR (400 MHz, DMSO) δ 7.81 (d, J=4.2 Hz, 4H), 7.45 (d, J=8.5 Hz, 4H), 7.36 (t, J=9.7 Hz, 4H), 7.25 (dd, J=16.2, 8.0 Hz, 12H), 6.34 (s, 2H).

Example 3

Preparation of Cyclic Compound 3: DBCZ

Type I tertiary alcohol synthon 1 (DBDFOH, 100 mg, 0.228 mmol) and carbazole (38.1 mg, 0.228 mmol) were quantitatively weighed, and put into a 500 mL reaction flask, and dried dichloromethane (228 mL) was added to the 500 mL reaction flask, and they were stirred to be uniform. When the substrates were fully dissolved, 0.2 mL of trifluoromethanesulfonic acid was added into the 500 mL reaction flask, stirred to be uniform, and the reaction was monitored by thin layer chromatography until the disappearance of the starting materials. When the reaction was completed, lye was added to quench the reaction, to obtain a reaction mixture. The reaction mixture was extracted with dichloromethane, and the organic phase was collected, dried with anhydrous magnesium sulfate, filtered out the desiccant, and distilled under reduced pressure to remove the solvent, to obtain a crude product. The crude product was further purified by silica gel column chromatography, to obtain a white solid powder (51 mg, 20%), which was confirmed by 1HNMR with the following data:

1H NMR (600 MHz, $CDCl_3$) δ 8.09 (d, J=8.7 Hz, 8H), 7.94 (d, J=8.0 Hz, 8H), 7.54 (t, J=8.3 Hz, 9H), 7.47 (t, J=7.1 Hz, 8H), 7.24 (s, 12H), 6.75 (d, J=7.0 Hz, 8H).

Example 4

Preparation of Cyclic Compound 4: 2-BrDBCZ

Type I tertiary alcohol synthon 1 (DBDFOH, 200 mg, 0.456 mmol) and 2-bromocarbazole (112 mg, 0.456 mmol) were quantitatively weighed, and put into a 1000 mL reaction flask, and dried dichloromethane (456 mL) was added into the 1000 mL reaction flask, and they were stirred to be uniform. When the substrates were fully dissolved, 0.4 mL of trifluoromethanesulfonic acid was added into the reaction flask, stirred to be uniform, and the reaction was monitored by thin layer chromatography until the disappearance of the starting materials. When the reaction was completed, lye was added to quench the reaction, to obtain a reaction mixture. The reaction mixture was extracted with dichloromethane, and the organic phase was collected, dried with anhydrous magnesium sulfate, filtered out the desiccant, and distilled under reduced pressure to remove the solvent, to obtain a crude product. The crude product was further purified by silica gel column chromatography, to obtain a white solid powder (150 mg, 50%), which was confirmed by 1HNMR with the following data:

$^1$H NMR (400 MHz, CDCl$_3$) δ 7.91 (q, J=5.6 Hz, 2H), 7.82 (d, J=11.5 Hz, 4H), 7.73 (d, J=8.7 Hz, 4H), 7.59-7.51 (m, 4H), 7.47 (t, J=8.3 Hz, 4H), 7.41 (t, J=6.4 Hz, 6H), 7.32 (dd, J=16.0, 12.8 Hz, 19H), 7.24 (s, 2H), 7.00 (d, J=8.3 Hz, 2H), 6.95 (d, J=5.9 Hz, 2H), 6.18 (d, J=20.4 Hz, 2H).

Example 5

Preparation of Cyclic Compound 5: 3-BrDBCZ

Type I tertiary alcohol synthon 1 (DBDFOH, 100 mg, 0.228 mmol) and 3-bromocarbazole (56 mg, 0.228 mmol) were quantitatively weighed, and put into a 1000 mL reaction flask, and dried dichloromethane (228 mL) was added into the 1000 mL reaction flask, and they were stirred to be uniform. When the substrates were fully dissolved, 0.2 mL of trifluoromethanesulfonic acid was added into the reaction flask, stirred to be uniform, and the reaction was monitored by thin layer chromatography until the disappearance of the starting materials. When the reaction was completed, lye was added to quench the reaction, to obtain a reaction mixture. The reaction mixture was extracted with dichloromethane, and the organic phase was collected, dried with anhydrous magnesium sulfate, filtered out the desiccant, and distilled under reduced pressure to remove the solvent. The crude product was further purified by silica gel column chromatography, to obtain a white solid powder (60 mg, 40%), which was confirmed by $^1$HNMR with the following data:

$^1$H NMR (400 MHz, CDCl$_3$) δ 7.93 (d, J=7.2 Hz, 2H), 7.82 (d, J=7.4 Hz, 4H), 7.74 (d, J=7.5 Hz, 4H), 7.68 (s, 2H), 7.56 (dd, J=7.6, 3.2 Hz, 4H), 7.50-7.45 (m, 4H), 7.41 (t, J=7.4 Hz, 4H), 7.34 (s, 9H), 7.30-7.26 (m, 10H), 7.22 (s, 2H), 7.18 (d, J=8.7 Hz, 2H), 6.67 (dd, J=8.7, 5.5 Hz, 2H), 6.25 (s, 1H), 6.18 (s, 1H).

Example 6

Preparation of Cyclic Compound 6: LBCZ

Type I tertiary alcohol synthon 2 (LBDFOH, 100 mg, 0.19 mmol) and carbazole (32 mg, 0.19 mmol) were quantitatively weighed, and put into a 500 mL reaction flask, and dried dichloromethane (190 mL) was added to the 500 mL reaction flask, and they were stirred to be uniform. When the substrates were fully dissolved, 0.3 mL of boron trifluoride ether was added to the 500 mL reaction flask, stirred to be uniform, and the reaction was monitored by thin layer chromatography until the disappearance of the starting materials. When the reaction was completed, lye was added to quench the reaction, to obtain a reaction mixture. The reaction mixture was extracted with dichloromethane, and the organic phase was collected, dried with anhydrous magnesium sulfate, filtered out the desiccant, and distilled under reduced pressure to remove the solvent, to obtain a crude product. The crude product was further purified by silica gel column chromatography, to obtain a white solid powder (30 mg, 23%), which was confirmed by $^1$HNMR with the following data:

$^1$H NMR (600 MHz, CDCl$_3$) δ 8.07 (d, J=8.2 Hz, 8H), 7.94 (t, J=3.0 Hz, 2H), 7.92 (d, J=8.0 Hz, 8H), 7.55 (d, J=6.9 Hz, 8H), 7.51 (t, J=7.7 Hz, 8H), 7.44 (d, J=8.0 Hz, 8H), 6.14 (d, J=87.0 Hz, 20H).

Example 7

Preparation of Cyclic Compound 7: 2-BrLBCZ

Type I tertiary alcohol synthon 2 (LBDFOH, 200 mg, 0.388 mmol) and 2-bromocarbazole (95 mg, 0.388 mmol) were quantitatively weighed, and put into a 500 mL reaction flask, and dried dichloromethane (389 mL) was added into the 500 mL reaction flask, and they were stirred to be uniform. When the substrates were fully dissolved, 0.34 mL trifluoromethanesulfonic acid was added to the reaction flask, stirred to be uniform, and the reaction was monitored by thin layer chromatography until the disappearance of the starting materials. When the reaction was completed, lye was added to quench the reaction, to obtain a reaction mixture. The reaction mixture was extracted with dichloromethane, and the organic phase was collected, dried with anhydrous magnesium sulfate, filtered out the desiccant, and distilled under reduced pressure to remove the solvent, to obtain a crude product. The crude product was further purified by silica gel column chromatography, to obtain a white solid powder (100 mg, 35%), which was confirmed by $^1$HNMR with the following data:

$^1$H NMR (400 MHz, CDCl$_3$) δ 7.87 (ddd, J=13.1, 8.2, 2.6 Hz, 6H), 7.79 (dd, J=7.0, 3.1 Hz, 4H), 7.58-7.51 (m, 8H), 7.48 (s, 2H), 7.46 (s, 3H), 7.43 (d, J=2.9 Hz, 2H), 7.35 (dddd, J=17.2, 15.4, 10.2, 4.8 Hz, 29H), 7.03 (dd, J=8.4, 1.6 Hz, 2H), 7.00-6.97 (m, 2H), 6.28 (s, 1H), 6.25 (s, 1H).

Example 8

Preparation of Cyclic Compound 8: 3-BrLBCZ

Type I tertiary alcohol synthon 2 (LBDFOH, 200 mg, 0.388 mmol) and 3-bromocarbazole (95 mg, 0.388 mmol) were quantitatively weighed, and put into a 500 mL reaction flask, and dried dichloromethane (389 mL) was added into the 500 mL reaction flask, and they were stirred to be uniform. When the substrates were fully dissolved, 0.34 mL trifluoromethanesulfonic acid was added to the reaction flask, stirred to be uniform, and the reaction was monitored by thin layer chromatography until the disappearance of the starting materials. When the reaction was completed, lye was added to quench the reaction, to obtain a reaction mixture. The reaction mixture was extracted with dichloromethane, and the organic phase was collected, dried with anhydrous magnesium sulfate, filtered out the desiccant, and distilled under reduced pressure to remove the solvent, to obtain a crude product. The crude product was further purified by silica gel column chromatography, to obtain a white solid powder (100 mg, 35%), which was confirmed by $^1$HNMR with the following data:

$^1$H NMR (400 MHz, CDCl$_3$) δ 7.92-7.83 (m, 6H), 7.80 (dd, J=7.0, 3.9 Hz, 4H), 7.72 (s, 2H), 7.54 (dd, J=15.9, 7.5 Hz, 8H), 7.44 (dd, J=16.5, 8.8 Hz, 8H), 7.39-7.34 (m, 15H), 7.34-7.26 (m, 12H), 7.21 (d, J=1.9 Hz, 1H), 7.19 (d, J=1.9 Hz, 1H), 6.72 (d, J=3.3 Hz, 1H), 6.69 (d, J=3.2 Hz, 1H), 6.30 (s, 1H), 6.27 (s, 1H).

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. A cyclic compound formed by a Friedel-Crafts reaction at positions 1 and 3 of carbazole, wherein the cyclic compound has a general structural formula of

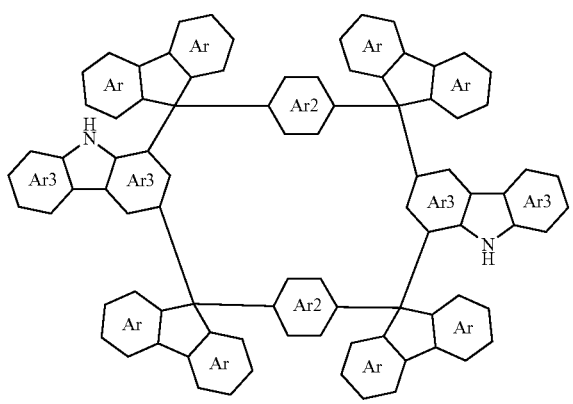

in which

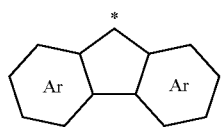

is selected from the group consisting of

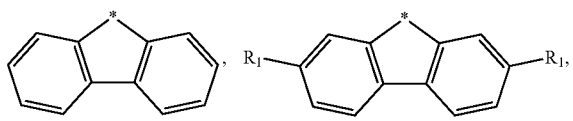

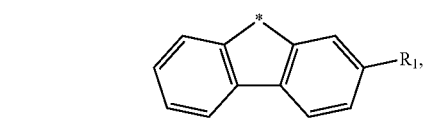

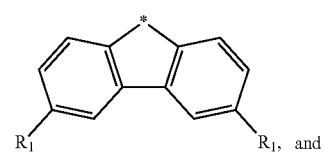

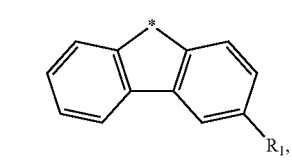

wherein $R_1$ is selected from the group consisting of an alkoxy, an alkyl, and a halogen,

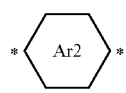

is selected from the group consisting of

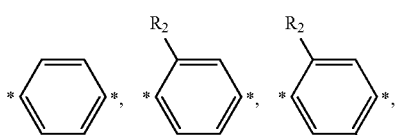

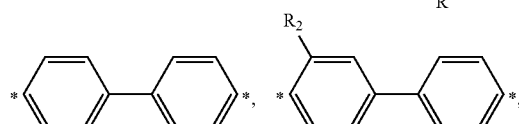

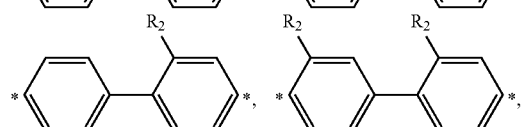

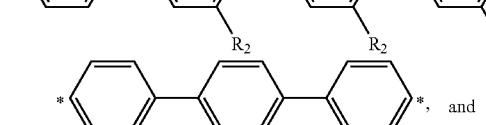

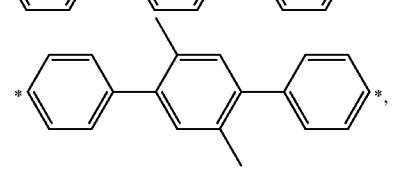

wherein $R_2$ is selected from the group consisting of an alkoxy, and an alkyl containing not more than 5 carbon atoms, and

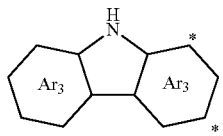

is selected from the group consisting of

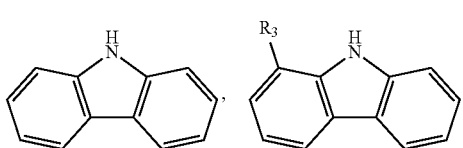

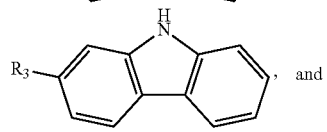

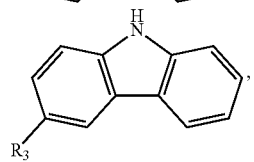

wherein $R_3$ is selected from the group consisting of an alkoxy, an alkyl, Br, and Cl.

2. The cyclic compound of claim 1, wherein the alkyl of $R_1$, $R_2$ and $R_3$ is tert-butyl.

* * * * *